United States Patent
Paul et al.

(10) Patent No.: US 11,808,830 B2
(45) Date of Patent: Nov. 7, 2023

(54) DETERMINING K-SPACE SAMPLING WITH SEMAC RECORDINGS

(71) Applicant: Siemens Healthcare GmbH, Erlangen (DE)

(72) Inventors: Dominik Paul, Bubenreuth (DE); Flavio Carinci, Würzburg (DE); Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 24 days.

(21) Appl. No.: 17/399,023

(22) Filed: Aug. 10, 2021

(65) Prior Publication Data
US 2022/0050159 A1 Feb. 17, 2022

(30) Foreign Application Priority Data
Aug. 11, 2020 (DE) ............ 10 2020 210 169.8

(51) Int. Cl.
*G01R 33/483* (2006.01)
*G01R 33/48* (2006.01)
*G01R 33/565* (2006.01)
*A61B 5/055* (2006.01)

(52) U.S. Cl.
CPC ..... *G01R 33/4835* (2013.01); *G01R 33/4818* (2013.01); *G01R 33/56536* (2013.01); *A61B 5/055* (2013.01)

(58) Field of Classification Search
CPC ............ A61B 5/055; G01R 33/4818; G01R 33/4835; G01R 33/56536
See application file for complete search history.

(56) References Cited

U.S. PATENT DOCUMENTS

2014/0266191 A1 9/2014 Sveinsson et al.
2015/0285890 A1* 10/2015 Bachschmidt ... G01R 33/56536
324/309

(Continued)

OTHER PUBLICATIONS

"Method for determining SEMAC steps for workflow automation"Idea: Dr. Paul Dominik, DE Erlangen; Dr. Mario Zeller, DE Erlangen; Flavio Carinci, DE Erlangen. 2021. pp. 1-4.

(Continued)

*Primary Examiner* — Gregory H Curran
(74) *Attorney, Agent, or Firm* — Lempia Summerfield Katz LLC (57) ABSTRACT

Acquisition of MR data with a compressed sensing technique in a volume section includes ascertaining an extent of magnetic field distortion within the volume section. A first gradient along a first direction is switched. An RF excitation pulse is radiated for selective excitation of a slice in the volume section while the first gradient is switched. The MR data is acquired in a volume of the volume section that is composed of the slice, a partial volume above the slice, and a partial volume below the slice by executing the following multiple times: switching a first phase-encoding gradient along a second direction; switching a second phase-encoding gradient along the first direction; and reading out the MR data in a k-space line while a readout gradient is switched along a readout direction. A set of k-space lines to be read out for the volume is determined in dependence on the extent.

20 Claims, 4 Drawing Sheets

(56) References Cited

U.S. PATENT DOCUMENTS

| | | | |
|---|---|---|---|
| 2016/0154080 A1* | 6/2016 | Wiens | G01R 33/246 324/309 |
| 2018/0017651 A1 | 1/2018 | Hey | |
| 2018/0292496 A1* | 10/2018 | Kaushik | A61B 5/055 |

OTHER PUBLICATIONS

German Office Action for German Application No. 10 2020 210 169.8 dated May 31, 2021.

Otazo, Ricardo, et al. "Sparse-SEMAC: rapid and improved SEMAC metal implant imaging using SPARSE-SENSE acceleration." Magnetic resonance in medicine 78.1 (2017): 79-87.

Worters, Pauline W., et al. "Compressed-sensing multispectral imaging of the postoperative spine." Journal of Magnetic Resonance Imaging 37.1 (2013): 243-248.

* cited by examiner

DETERMINING K-SPACE SAMPLING WITH SEMAC RECORDINGS

This application claims the benefit of German Patent Application Number 10 2020 210 169.8, filed on Aug. 11, 2020, which is hereby incorporated by reference in its entirety.

BACKGROUND

The present embodiments relate to determination of k-space sampling with slice encoding for metal artifact correction (SEMAC) recording using the compressed sensing technique.

Herein, compressed sensing or compressed sampling may be a statistical technique for data acquisition that aims to sample only a comparatively small number of measuring points in k-space. These measured values or k-space lines that are sparsely acquired in k-space may, under certain conditions, reproduce almost all the information that, without compressed sampling, may only be reconstructed by acquiring all the measuring points in k-space.

To suppress metal artifacts (e.g., in the slice direction), the SEMAC method is, for example, used with spin-echo sequences (e.g., turbo spin-echo sequences). Herein, (e.g., with conventional 2D protocols) additional encoding in the slice direction is used. This encoding is similar to phase encoding and is frequently referred to as SEMAC encoding. With this additional SEMAC encoding, the measurement time increases linearly with the number of SEMAC steps required to perform the SEMAC encoding, as explained in the following example.

Without SEMAC encoding, a measurement with 256 phase-encoding steps with a turbo factor of 8 and a TR of 2000 ms requires a measurement time TA according to the following equation.

$$TA = 256/8 \cdot 2 \; s = 64 \; s = 1{:}04 \; min$$

If the SEMAC method with a SEMAC resolution of 15 steps is selected to suppress metal artifacts in one variant of this measurement, this measurement time TA increases by a factor of 15 and thus to more than 15 minutes. In addition, the image quality is dependent on the metal artifacts.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a variant of the SEMAC method with which the image quality is improved compared to the conventional variant of the SEMAC method is provided.

The present embodiments provide a method for acquiring magnetic resonance (MR) data in a predetermined volume section of an examination object using a magnetic resonance system. Herein, the MR data is acquired by compressed sensing. The method according to the present embodiments includes the following acts.

An extent of magnetic field distortion within the volume section is ascertained. The extent of the magnetic field distortion is, for example, determined based on the results or output of a scout measurement (e.g., a SEMAC scout measurement). To ascertain this extent or to ascertain these results, it is, for example, possible for a scout measurement to be performed before the further acts. A scout measurement is used to obtain information on the extent of distortion, for example, due to a metal implant in the examination object.

A first gradient (e.g., a slice selection gradient) is switched along a first direction.

An RF excitation pulse is radiated for the selective excitation of a slice in the volume section while the first gradient is switched.

The MR data is acquired in a volume composed of the following parts: the excited slice, a partial volume above the slice, and a partial volume below the slice (e.g., which has a same extent as the partial volume above the slice).

Herein, a length between the midpoint of the partial volume above the slice and the midpoint of the partial volume below the slice is, for example, perpendicular to the slice. The MR data in this volume is acquired by executing the following acts multiple times.

A first phase-encoding gradient is switched along a second direction.

A second phase-encoding gradient or SEMAC encoding gradient is switched along the first direction.

The MR data is read out in a k-space line while a readout gradient is switched along a readout direction.

Herein, the first direction, the second direction, and the readout direction are mutually perpendicular in each case.

A set of k-space lines to be read out for the volume is determined in dependence on the extent of the magnetic field distortion.

Determining the set of k-space lines to be read out for the volume in dependence on the extent of the magnetic field distortion enables this set of k-space lines to be optimally adapted to the individual extent of the magnetic field distortion (e.g., caused by the individual metal implant in the examination object) ascertained, for example, on the basis of the results of the scout measurement in order to achieve a measurement with a sufficiently good signal-noise ratio or with good image quality with as few k-space lines as possible. In other words, the set of k-space lines may be adapted to the actual distortion of the individual implant and/or the material-specific properties of the respective examination object in order to achieve good image quality during the measurement. Hence, the advantage of the present embodiments consists of adapting the set of k-space lines to the concrete or patient-specific situation.

With the method according to the present embodiments, a slice is excited in the volume section, and the MR data of the associated volume is acquired in the described manner (e.g., such a number of times until the entire volume section has been sampled).

Herein, the set of k-space lines to be read out for the volume (e.g., respective volume) may be determined by: the number of k-space lines to be read out for the volume; and/or the first phase-encoding gradient and the second phase-encoding gradient to be switched when the k-space lines are read out. These phase-encoding gradients are used, for example, to determine the position of the respective k-space line in k-space In other words, two sets of k-space lines may differ with respect to the number and/or with respect to the position of their k-space lines.

In an embodiment, the number of k-space lines to be read out for the volume is predetermined or constant so that only the position or distribution of the k-space lines in k-space is determined (e.g., optimized) in dependence on the extent of the magnetic field distortion.

In addition, the k-space lines to be read out for the volume are, for example, randomly (e.g., pseudo-randomly) distributed.

According to one embodiment, a density function is defined or determined in a plane (e.g., surface) of the k-space perpendicular to the readout direction in dependence on the extent of the magnetic field distortion. The density function specifies a density for each point in this plane (e.g., surface) that lies in k-space. The density function is symmetrical. The density function has one or more maximum values, for example, for a mean value of the second phase-encoding gradient or SEMAC encoding gradient corresponding to half the sum of the maximum value and the minimum value of the second phase-encoding gradient. Herein, the maximum value corresponds to a k-space point on a first edge of the k-space, and the minimum value corresponds to a k-space point on a second edge of the k-space that is opposite the first edge.

A density of the k-space lines to be read out for the volume corresponds to the density function. In other words, the number of k-space lines for a surface in the plane is proportional to a mean value obtained from the density according to the density function for this surface.

For example, the density function or density distribution may correspond to a Poisson distribution (e.g., Poisson Disk) or a Gaussian distribution.

The density function is a very good way of describing the extent of magnetic field distortion. In the case of weak distortion, the density function decreases more rapidly starting from a maximum of the density function, whereas the density function decreases more slowly in the case of strong distortion. Thus, by determining the k-space lines to be acquired for the volume on the basis of the density function, in the case of weak distortion, proportionally more k-space lines are acquired in the vicinity of the maximum, and thus in the vicinity of the k-space center, than in the case of greater distortion with which hence more k-space lines or MR data are acquired at a greater distance from the slice.

The present embodiments make it possible, for example, for fewer k-space lines or less MR data to be sampled for the respective volume in the case of lower distortion of the magnetic field than in the case of greater distortion. Herein, for example, the same number of k-space lines or amount of MR data may be sampled in the vicinity of the k-space center regardless of the extent of the distortion. Only in the case of lower distortion may fewer k-space lines or less MR data (e.g., determined by the density function in each case) be sampled at the edge of the k-space than in the case of strong distortion. Herein, it is, for example, assumed that the k-space is of the same size regardless of the extent of the distortion.

Since the MR data is acquired based on k-space lines (e.g., the MR data is in each case acquired with switched phase gradients in one step along the readout direction), the density function, for example, specifies a density for each point of the plane perpendicular to the readout direction, which, for example, includes the k-space center. In one embodiment, the following variants exist with respect to the symmetry properties of the density function.

In the first variant, the density function is symmetrical to an axis that is perpendicular to the plane and passes through the middle of the k-space. Herein, the density function has a maximum at this middle or this midpoint. The density (and thus the density of the k-space lines) determined by the density function decreases as the distance from the midpoint increases.

In the second variant, the density function is symmetrical to a further plane that is perpendicular to the plane and the SEMAC encoding direction or first direction. The further plane also divides the k-space into two halves. Herein, in the second variant, the density function has a maximum at a distance lying on a straight line corresponding to the intersection of the plane with the further plane and bounded by opposite edges of the k-space. The density function is symmetrical to this further plane or this length, and the density (and thus the density of the k-space lines) decreases as the distance from this length increases.

The density function may also be staggered. This provides the number of k-space lines to be read out for the volume changes abruptly (e.g., in dependence on the above-described distance). For this purpose, for example, the density of the k-space lines may be kept constant for certain distance intervals so that the density only changes at the distance interval limits.

According to one embodiment, the density function p obeys the following equation (1).

$$p(x) = \frac{1}{\sqrt{2\pi I^2}} e\left(-\frac{x^2}{2I^2}\right), \quad (1)$$

Herein, x corresponds to the distance from the midpoint in the first variant and to the distance from the length in the second variant. The factor I (also known as standard deviation) is determined in dependence on the extent of the magnetic field distortion.

Herein, for example, the greater I is selected, the greater the extent of the magnetic field distortion.

According to the present embodiments, further slices may be defined parallel to the slice. Half of these further slices are located below the slice, and the other half of the further slices is located above the slice. The further slices are arranged together with the slice such that a distance between any two adjacent slices (e.g., directly adjacent slices) is the same in each case. It is determined in dependence on the extent of the magnetic field distortion up to which of the further slices, starting from the slice, k-space lines or MR data are to be acquired as a maximum. Herein, a corresponds to the number of further slices that exist from the slice up to the slice to be acquired as a maximum.

In conventional SEMAC methods, a corresponds to half a number of SEMAC steps (e.g., of further slices to be sampled in addition to the slice). The higher a is determined, the stronger the extent of the magnetic field distortion and the greater the number of k-space lines that are to be acquired for the respective volume. The lower a is determined, the weaker the extent of the magnetic field distortion and the lesser the number of k-space lines that are to be acquired for the respective volume. The number of k-space lines to be sampled for the respective volume is, for example, proportional to a.

According to one variant, the factor I may be determined based on a factor s, where s is determined by the following equation (2).

$$s = \frac{a}{0.5 \cdot A} \quad (2)$$

Herein, A corresponds to the total number of further slices. The factor I is determined in dependence on the factor s.

Since, as a rule, according to equation (2), the greater s is, the greater the extent of the magnetic field distortion, this provides that the greater s is, the greater I may be determined, for example.

Herein, the factor I may, for example, be determined according to the following equation (3), where m and t>0.

$$I = m \cdot s + t \tag{3}$$

In other words, the factor I increases linearly with the factor s.

A good choice is, for example, m=15/8 and t=9/8. With this choice, for s=0.2, I=1.5, and for s=1 (e.g., the distortion extends to the last further slice), I has a rather large value of 3.

As already mentioned above, for example, a slice in the volume section is excited, and the MR data of the associated volume is acquired in the described manner (e.g., such a number of time until the MR data of the entire volume section has been acquired). According to a further embodiment, the set of k-space lines to be read out for the volume for the respective slice is determined individually for each of these slices. This provides that, for example, the density function is determined individually for each of these slices.

This embodiment enables account to be taken of the fact that, the further away from an implant the respective slice is located, the lower the extent of the magnetic field distortion caused by the implant.

The present embodiments also provide a magnetic resonance system for acquiring MR data from a predetermined volume section of an examination object with the aid of compressed sensing. Herein, the magnetic resonance system includes an RF control unit, a gradient control unit, an image-sequence control system, and a calculating unit (e.g., together including one or more processors), and is configured to ascertain an extent of magnetic field distortion within the volume section. The magnetic resonance system is also configured to switch a first gradient along a first direction with a gradient control unit of the magnetic resonance system in order to radiate an RF excitation pulse for the selective excitation of a slice within the volume section with the RF control unit while the first gradient is switched, and to acquire MR data in a volume that is composed of the slice, a partial volume below the slice, and a partial volume above the slice. To acquire the MR data in the volume, the magnetic resonance system is also configured to perform the following multiple times: switch a first phase-encoding gradient along a second direction; switch a second phase-encoding gradient or SEMAC gradient along the first direction; and read out the MR data along a k-space line while a readout gradient is switched along a readout direction. Herein, the first direction, the second direction, and the readout direction are mutually perpendicular. Herein, the magnetic resonance system is configured to use a calculating unit of the magnetic resonance system to determine a set of k-space lines to be read out for the volume in dependence on the extent of the magnetic field distortion.

Herein, the advantages of the magnetic resonance system according to the present embodiments substantially correspond to the advantages of the method according to the present embodiments, which were explained in detail above and so will not be repeated here.

The present embodiments also describe a computer program product (e.g., a computer program or software) that may be loaded into a memory of a programmable control system or calculating unit of a magnetic resonance system. The computer program product is able to execute all or some of the above-described embodiments of the method according to the present embodiments when the computer program product runs in the control system or control facility of the magnetic resonance system. Herein, the computer program product may require program means (e.g., libraries and auxiliary functions) in order to implement the corresponding embodiments of the method. In other words, claims directed to the computer program product is, for example, intended to protect a computer program or software with which one of the above-described embodiments of the method according to the present embodiments may be executed or which executes this embodiment. Herein, the software may be a source code (e.g., C++) that is still to be compiled (e.g., translated) and linked or only has to be interpreted, or an executable software code that is to be loaded into the corresponding calculating unit or control facility.

The present embodiments also include an electronically readable data carrier (e.g., a non-transitory computer-readable storage medium; a DVD, a magnetic tape, a hard disk, or a USB stick), on which electronically readable control information (e.g., software (see above)) is stored. When this control information (e.g., software) is read from the data carrier and stored in a control facility or calculating unit of a magnetic resonance system, all of the embodiments according to the present embodiments of the above-described method may be performed.

With the present embodiments, the number and distribution of the points to be recorded in k-space are not rigid or fixed, but are adapted to the actual extent of the magnetic field distortion. Thus, this distribution of k-space points or k-space lines may be optimally adapted to the actual distortion of a certain implant, and the image quality may be optimized in a material-specific manner. In other words, the quality of an image generated with the MR data acquired may be optimized in dependence on the concrete situation and thus patient-specifically.

Thus, the present embodiments are able to optimally distribute the k-space lines in dependence on an underlying magnetic field distortion. The number of k-space lines or amount of MR data to be acquired may also be adapted to the extent of magnetic field distortion without any excessive negative influence of a signal-noise ratio.

DETAILED DESCRIPTION

Figure 1:
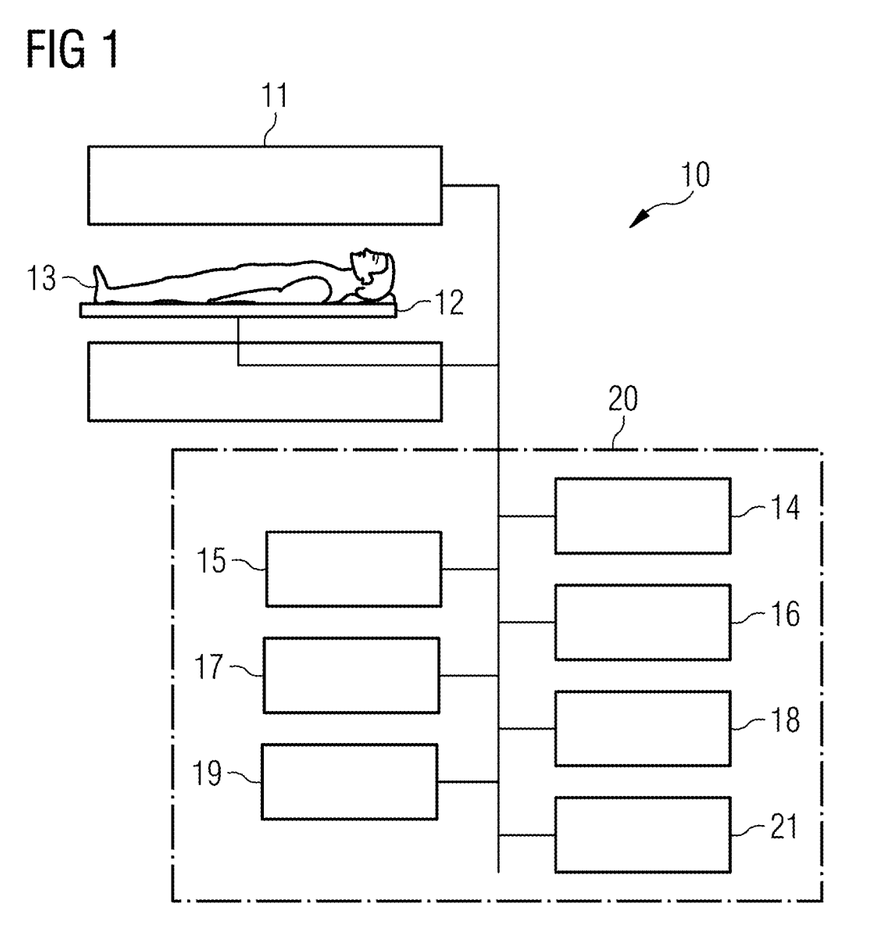
FIG. 1 is a schematic depiction of one embodiment of a magnetic resonance system.

With reference to FIG. 1, a magnetic resonance system 10 is depicted, with which, as will be explained below, magnetic resonance (MR) data is acquired according to the present embodiments using a SEMAC method. The magnetic resonance system 10 has a magnet 11 for generating a polarization field BO. An examination subject 13 arranged on a couch 12 is moved into the magnet 11 where spatially encoded magnetic resonance signals or MR data from the examination subject 13 are to be recorded. The coils used for the signal recording, such as a whole-body coil or local coils, are not shown for reasons of clarity. Radiation of radio-frequency (RF) pulses and switching of (e.g., applying) magnetic field gradients enables magnetization generated by the polarization field BO to be deflected from an equilibrium position and spatially encoded, and the resulting magnetization is detected by the receiving coils. The way in which MR images may be generated by radiation of the RF pulses and switching of (e.g., applying) magnetic field gradients in different combinations and sequences is known in principle to the person skilled in the art and will not be explained in any further detail here.

The magnetic resonance system 10 also has a control unit 20 that may be used to control the magnetic resonance system 10. The control system 20 has a gradient control unit 15 for controlling and switching necessary magnetic field gradients. An RF control unit 14 is provided to control and generate the RF pulses to deflect the magnetization. An image-sequence control system 16 controls the sequence of magnetic field gradients and RF pulses and thus indirectly the gradient control unit 15 and the RF control unit 14. An operator may control the magnetic resonance system 10 via an input unit 17, and MR images and other information necessary for the control may be displayed on a display unit 18. A calculating unit 19 with at least one processor unit (not shown) is provided to control the different units in the control unit 20 and to perform calculation operations. Further, a memory unit 21 is provided in which, for example, program modules or programs that, when executed by the calculating unit 19 or a corresponding processor unit, may control the sequence of the magnetic resonance system 10 may be stored. The calculating unit 19 is configured to calculate the MR images from the acquired MR signals.

Figure 2:
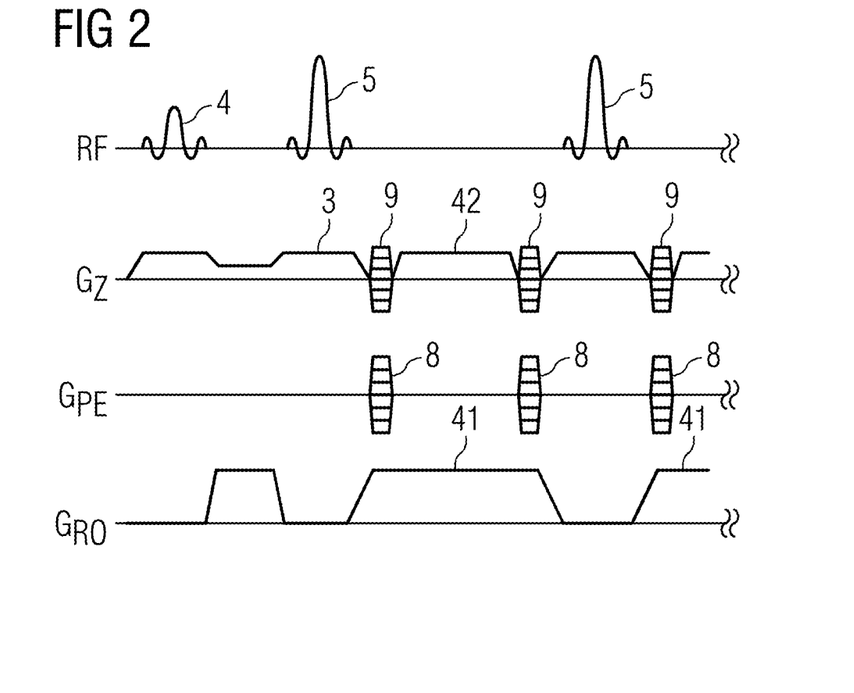
FIG. 2 depicts an exemplary sequence for acquiring magnetic resonance (MR) data.

FIG. 2 depicts an exemplary spin-echo sequence for the acquisition of MR data according to the present embodiments.

Figure 3:
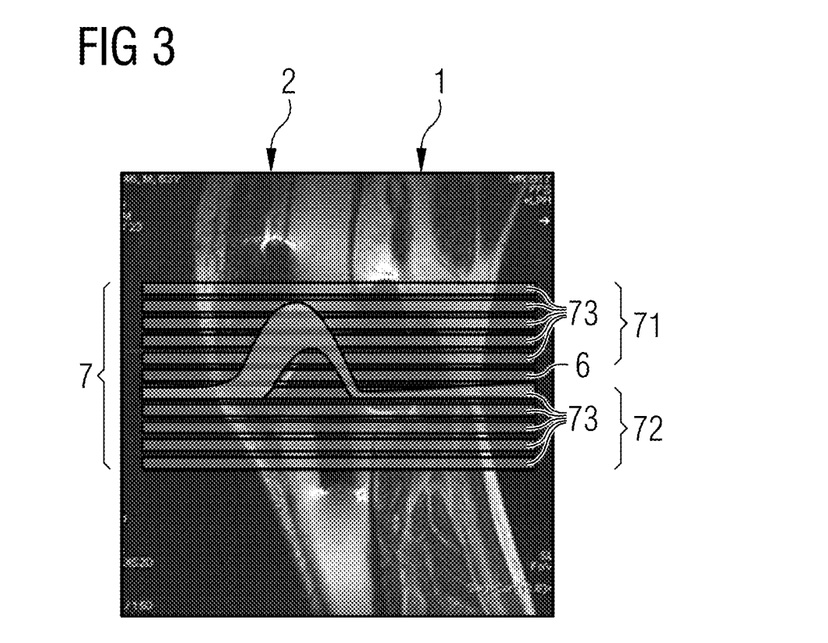
FIG. 3 is a depiction according to an embodiment of a volume to be acquired for an excited slice together with effects of magnetic field distortion.

An RF excitation pulse 4 and an RF refocusing pulse 5 are radiated while simultaneously a slice selection gradient 3 is switched in a slice selection direction or first direction Gz in order to excite a slice 6 (see FIG. 3). MR data is then acquired in a volume composed of the excited slice 6 and a partial volume above the slice 6 and a partial volume below the slice 6 (e.g., two partial volumes). The MR data in the two partial volumes is acquired in order also to detect signal components that are located outside the slice 6 due to magnetic field distortion caused, for example, by a metal implant.

The MR data in this volume is acquired by repeatedly switching a first phase-encoding gradient 8 and a SEMAC gradient or second phase-encoding gradient 9 along the first direction Gz after a refocusing pulse 5 in order to sample MR data along a readout direction $G_{RO}$ or along a k-space line while a readout gradient 41 is switched. Herein, a VAT gradient 42 may be switched between two successive SEMAC gradients 9 in each case.

FIG. 3 is intended to explain in more detail where and why the sequence outlined in FIG. 2 acquires MR data in the volume section of the examination object.

Although the slice 6 is excited in the volume section 1, magnetic field distortion 2 causes certain signal components to be located outside the slice 6. For this reason, according to the present embodiments, for each excited slice 6, MR data is also acquired in a partial volume 71 above the slice and in a partial volume 72 below the slice. In other words, MR data is acquired in a volume 7 composed of the partial volume 71 above the slice, the partial volume 72 below the slice, and the slice 6 itself.

Herein, the volume 7 may also be imagined as being composed of the slice 6 and further slices 73. In the case shown in FIG. 3, there are five further slices 73 above and five further slices below the excited slice 6. Since each further slice may also be referred to as a SEMAC encoding step, the case shown in FIG. 3 may correspond to a protocol with 10 SEMAC steps (in addition to the actual slice 6, which may be referred to as the SEMAC step). FIG. 3 also shows that the magnetic field distortion extends into the fourth further slice above the excited slice 6.

Herein, the MR data of the volume 7 is acquired based on k-space lines that are sampled along the readout direction. Herein, k-space lines are distributed in k-space in dependence on a density function.

Figure 4:
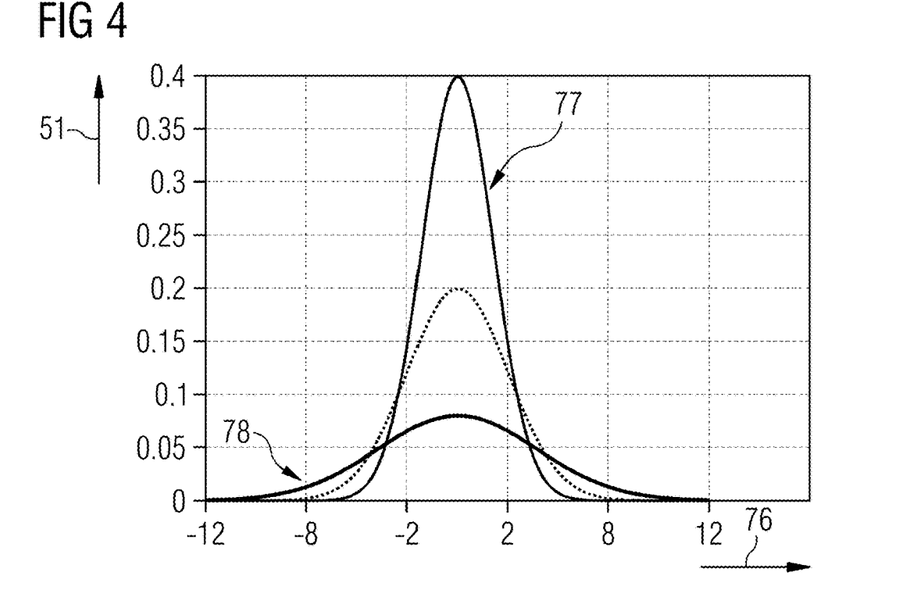
FIG. 4 is a depiction according to an embodiment of density distributions in dependence on the extent of magnetic field distortion.

Examples of this density function are depicted in FIG. 4. Herein, the density function 77, 78 is depicted by SEMAC steps 76 or by a SEMAC encoding direction 74 (see FIG. 5).

The density function 77, 78 depicted in FIG. 4 indicates in each case how the k-space lines are distributed in k-space.

Figure 5:
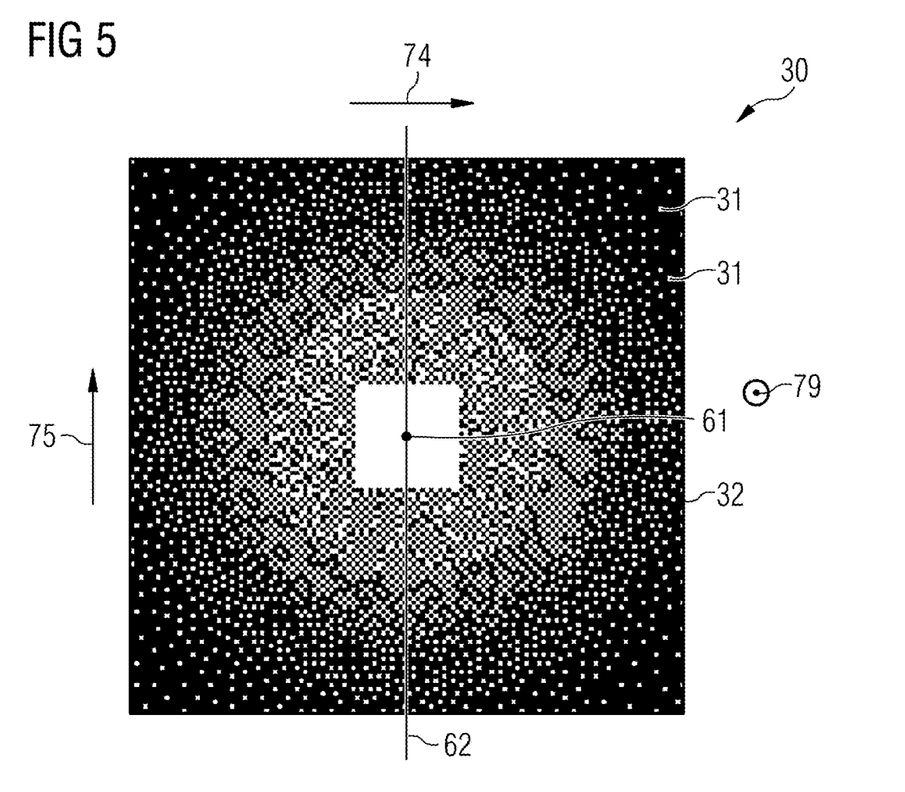
FIG. 5 depicts a distribution of k-space lines according to an embodiment.

FIG. 5 depicts an exemplary distribution of k-space lines 31 in k-space 30 for acquiring the MR data in the volume 7 for a slice 6. For this purpose, FIG. 5 depicts a k-space surface 32 perpendicular to the readout encoding 79 that is spanned by the SEMAC encoding 74 and the phase encoding 75. The middle 61 of this surface 32 also lies in a plane 62 that is perpendicular to the SEMAC encoding 74 and divides the k-space 30 and the surface 32 depicted into two halves (e.g., equal halves). As a result, the middle 61 of the surface 32 also corresponds to the k-space center.

The density of the k-space lines 31 is proportional to the density function 77, 78. This provides that the number of k-space lines per surface segment of the k-space surface 32 is proportional to the density 51 indicated by the density function 77, 78.

Herein, there are two variants.

In the first variant, the density function 77, 78 determined based on the extent of the magnetic field distortion is symmetrical to an axis that is perpendicular to the k-space surface 32 and passes through the midpoint 61. In this first variant, the density 51 is a function of distance from the midpoint 61 within the k-space surface 32.

In the second variant, the density function 77, 78 is symmetrical to the plane 62. Hence, in the second variant, the density 51 is a function of the distance from a length (e.g., within the k-space surface 32) resulting from the intersection of the plane 62 with the k-space surface 32.

In the embodiment depicted in FIG. 5, the volume in the middle of the k-space, which is defined based on the square in the middle of the k-space surface 32, is completely sampled. This provides that the density of the k-space lines within the square is 1 or 100%, so that, in this embodiment, the density of the k-space lines only corresponds to the density function outside the square or the density of the k-space lines (and thus the density function) is staggered.

Figure 6:
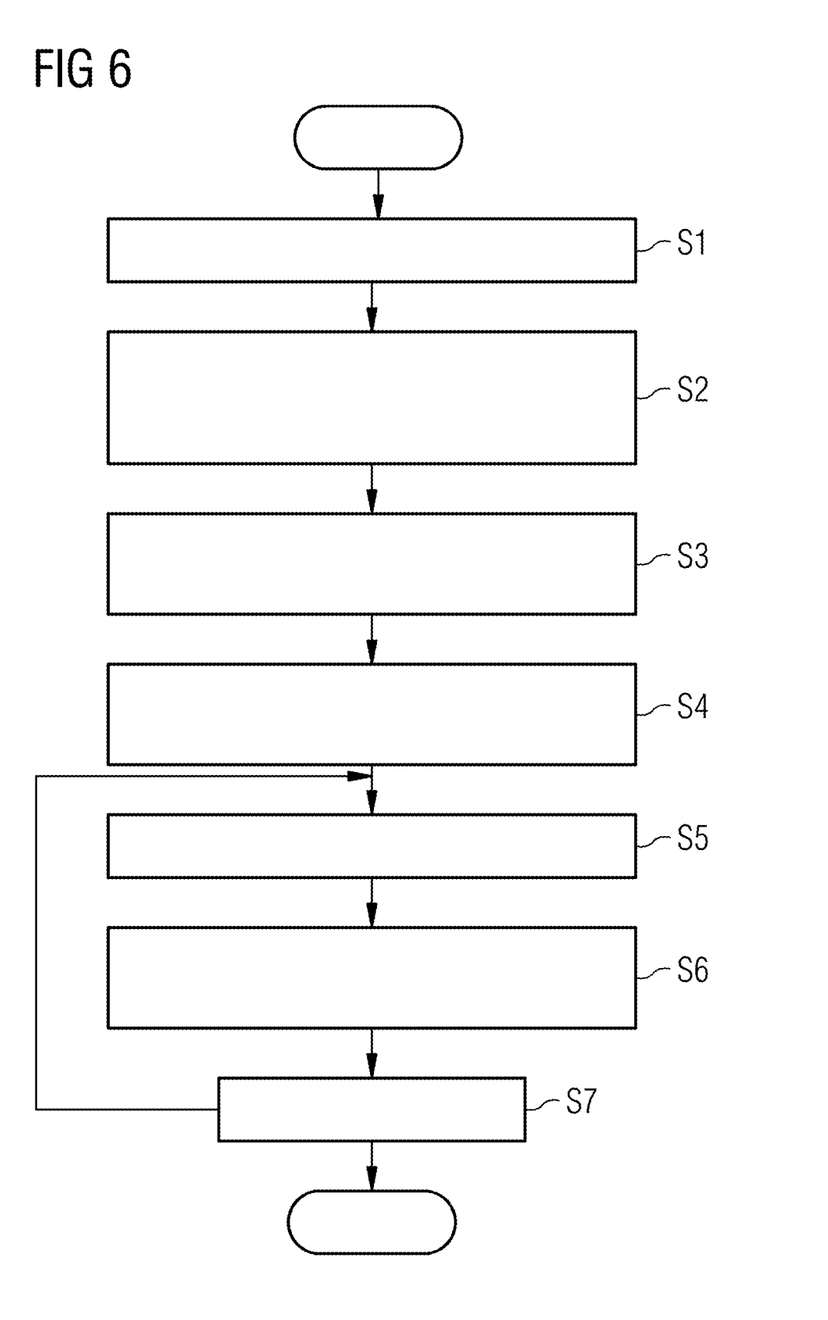
FIG. 6 is a flow diagram of a method according to an embodiment.

FIG. 6 depicts a flow diagram for a method according to the present embodiments.

In a first act S1, a scout measurement is performed in order to determine an extent of the magnetic field distortion in act S2 based on the results of the scout measurement. Act S1 may be omitted if the results of a scout measurement or the extent of the magnetic field distortion may be determined in some other way.

Based on the extent of the magnetic field distortion, in act S3, a density function is determined based on the basis of which the k-space lines to be recorded for each slice are then determined in act S4. In this act S4, the distribution of the k-space lines is, for example, determined based on the density function (e.g., proportional to the density function).

If the k-space lines or MR data to be acquired for each slice have been determined based on acts S1 to S4, this MR data may be acquired in the following acts. For this purpose, a slice is excited in act S5 in order then to acquire the MR data in act S6 by sampling the k-space lines determined. Acts S5 and S6 are repeated until MR data has been acquired for all slices in the predetermined volume section.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for acquiring magnetic resonance (MR) data with a compressed sensing technique in a predetermined volume section of an examination object using a magnetic resonance system, the method comprising:
   ascertaining an extent of magnetic field distortion within the predetermined volume section;
   applying a first gradient along a first direction;
   radiating a radio frequency (RF) excitation pulse for selective excitation of a slice in the volume section while the first gradient is applied; and
   acquiring the MR data in a volume of the volume section that is composed of the slice, a partial volume above the slice, and a partial volume, below the slice, the acquiring of the MR data comprising:
      applying a first phase-encoding gradient along a second direction;
      applying a second phase-encoding gradient along the first direction;
      reading out the MR data in a k-space line while a readout gradient is applied along a readout direction; and
      repeating the applying of the first phase-encoding gradient, the applying of the second phase-encoding gradient, and the reading out of the MR data multiple times,
   wherein the first direction, the second direction, and the readout direction are mutually perpendicular,
   wherein a set of k-space lines to be read out for the volume is determined in dependence on the extent of the magnetic field distortion, and
   wherein a density function specifies a density for each point in a plane of a k-space.

2. The method of claim 1, wherein the set of k-space lines to be read out for the volume is determined by a number of k-space lines to be read out for the volume, by the first phase-encoding gradient and the second phase-encoding gradient, which are applied when the respective k-space line is read out, or by a combination thereof.

3. The method of claim 1, wherein the set of k-space lines to be read out for the volume are randomly distributed.

4. The method of claim 1, wherein the density function is defined in the plane of the k-space perpendicular to readout encoding in dependence on the extent of the magnetic field distortion,
   wherein the density function is symmetrical, and
   wherein a density of the set of k-space lines to be read out for the volume corresponds to the density function.

5. The method of claim 4, wherein the density function is symmetrical to an axis that, in the middle, stands perpendicular to a surface in the k-space corresponding to the volume and is spanned by the direction of the first phase-encoding gradient and by the direction of the second phase-encoding gradient, and
   wherein the density function has a maximum in the middle of the surface, and
   wherein the density function decreases as a distance from the middle increases.

6. The method of claim 4, wherein the density function is symmetrical to the plane that, in the k-space corresponding to the volume, is perpendicular to a direction of the second phase-encoding gradient and divides the k-space into two halves,
   wherein the density function has a maximum at a length that lies in a k-space surface that is spanned by the direction of the first phase-encoding gradient and the direction of the second phase-encoding gradient, and in the plane, and
   wherein the density function decreases as a distance from the length increases.

7. The method of claim 4, wherein the density function corresponds to a Poisson distribution or a Gaussian distribution.

8. The method of claim 4, wherein the density function corresponds to the following equation:

$$p(x) = \frac{1}{\sqrt{2\pi I^2}} e^{\left(-\frac{x^2}{2I^2}\right)},$$

wherein x corresponds to a distance from a middle of the k-space or from a length in a k-space surface, and a factor I is determined in dependence on the extent of the magnetic field distortion.

9. The method of claim 1, wherein further slices are defined parallel to the slice,
   wherein a first half of the further slices are below the slice, and a second half of the further slices are above the slice,
   wherein the further slices are arranged together with the slice such that a distance between adjacent slices is the same,
   wherein the extent of the magnetic field distortion is used to determine up to which of the further slices MR data is to be acquired as a maximum,
   wherein a number a corresponds to a number of the further slices that are present from the slice up to the further slice to be acquired as a maximum, and
   wherein a number of the k-space lines to be read out for the volume is determined in dependence on the number a.

10. The method of claim 9, wherein a factor s is determined using the following equation:

$$s = \frac{a}{0.5 \cdot A},$$

wherein A corresponds to a total number of further slices, and the factor I is determined in dependence on s.

11. The method of claim 10, wherein the factor I is determined according to the following equation:

$$I = m \cdot s + t, \text{ and}$$

wherein m and t are positive constants.

12. The method of claim 11, wherein m=15/8 and t=9/8.

13. The method of claim 1, wherein applying the first gradient, radiating the RF excitation pulse, and acquiring the MR data in the volume are performed multiple times for multiple slices in the volume section, and
wherein the set of k-space lines to be read out for the respective volume is determined individually for each of the slices.

14. A magnetic resonance system for acquiring magnetic resonance (MR) data with a compressed sensing technique in a predetermined volume section of an examination object, the magnetic resonance system comprising:
a radio frequency (RF) control unit;
a gradient control unit;
an image-sequence control system; and
a calculating unit,
wherein the magnetic resonance system is configured to:
determine an extent of magnetic field distortion within the volume section;
apply a first gradient along a first direction with the gradient control unit;
radiate an RF excitation pulse for selective excitation of a slice in the volume section with the RF control unit while the first gradient is applied; and
acquire MR data in a volume of the volume section that is composed of the slice, a partial volume above the slice, and a partial volume below the slice, and
wherein the magnetic resonance system is further configured to:
apply a first phase-encoding gradient along a second direction;
apply a second phase-encoding gradient along the first direction; and
read out the MR data in a k-space line while a readout gradient is applied along a readout direction; and
repeat the application of the first phase-encoding gradient, the application of the second phase-encoding gradient, and the read out of the MR data multiple times,
wherein the first direction, the second direction, and the readout direction are mutually perpendicular,
wherein the magnetic resonance system is further configured to use the calculating unit to determine a set of k-space lines to be read out for the volume in dependence on the extent of the magnetic field distortion, and
wherein a density function specifies a density for each point in a plane of a k-space.

15. The magnetic resonance system of claim 14, wherein the density function is defined in the plane of the k-space perpendicular to readout encoding in dependence on the extent of the magnetic field distortion,
wherein the density function is symmetrical, and
wherein a density of the set of k-space lines to be read out for the volume corresponds to the density function.

16. In a non-transitory computer-readable storage medium that stores instructions executable by a control facility of a magnetic resonance system to acquire magnetic resonance (MR) data with a compressed sensing technique in a predetermined volume section of an examination object using the magnetic resonance system, the instructions comprising:
ascertaining an extent of magnetic field distortion within the predetermined volume section;
applying a first gradient along a first direction;
radiating a radio frequency (RF) excitation pulse for selective excitation of a slice in the volume section while the first gradient is applied; and
acquiring the MR data in a volume of the volume section that is composed of the slice, a partial volume above the slice, and a partial volume, below the slice, the acquiring of the MR data comprising:
applying a first phase-encoding gradient along a second direction;
applying a second phase-encoding gradient along the first direction;
reading out the MR data in a k-space line while a readout gradient is applied along a readout direction; and
repeating the applying of the first phase-encoding gradient, the applying of the second phase-encoding gradient, and the reading out of the MR data multiple times,
wherein the first direction, the second direction, and the readout direction are mutually perpendicular,
wherein a set of k-space lines to be read out for the volume is determined in dependence on the extent of the magnetic field distortion, and
wherein a density function specifies a density for each point in a plane of a k-space.

17. The non-transitory computer-readable storage medium of claim 16, wherein the density function is defined in the plane of the k-space perpendicular to readout encoding in dependence on the extent of the magnetic field distortion,
wherein the density function is symmetrical, and
wherein a density of the set of k-space lines to be read out for the volume corresponds to the density function.

18. The non-transitory computer-readable storage medium of claim 17, wherein the density function is symmetrical to an axis that, in the middle, stands perpendicular to a surface in the k-space corresponding to the volume and is spanned by the direction of the first phase-encoding gradient and by the direction of the second phase-encoding gradient, and
wherein the density function has a maximum in the middle of the surface, and
wherein the density function decreases as a distance from the middle increases.

19. The non-transitory computer-readable storage medium of claim 17, wherein the density function is symmetrical to the plane that, in the k-space corresponding to the volume, is perpendicular to a direction of the second phase-encoding gradient and divides the k-space into two halves,
wherein the density function has a maximum at a length that lies in a k-space surface that is spanned by the direction of the first phase-encoding gradient and the direction of the second phase-encoding gradient, and in the plane, and wherein the density function decreases as a distance from the length increases.

20. The non-transitory computer-readable storage medium of claim 17, wherein the density function corresponds to a Poisson distribution or a Gaussian distribution.

* * * * *